United States Patent
Bare

(10) Patent No.: US 9,205,110 B2
(45) Date of Patent: Dec. 8, 2015

(54) ENHANCED AUTOLOGOUS GROWTH FACTOR PRODUCTION AND DELIVERY SYSTEM

(71) Applicant: Arthrex, Inc., Naples, FL (US)

(72) Inventor: Christopher M. Bare, Naples, FL (US)

(73) Assignee: Arthrex, Inc., Naples, FL (US)

( * ) Notice: Subject to any disclaimer, the term of this patent is extended or adjusted under 35 U.S.C. 154(b) by 198 days.

(21) Appl. No.: 13/941,899

(22) Filed: Jul. 15, 2013

(65) Prior Publication Data

US 2014/0023720 A1    Jan. 23, 2014

Related U.S. Application Data

(60) Provisional application No. 61/672,975, filed on Jul. 18, 2012.

(51) Int. Cl.
| | | |
|---|---|---|
| *A01N 1/02* | (2006.01) | |
| *C12N 5/00* | (2006.01) | |
| *C12N 5/02* | (2006.01) | |
| *A61K 35/16* | (2015.01) | |
| *A61K 35/12* | (2015.01) | |

(52) U.S. Cl.
CPC ............ *A61K 35/16* (2013.01); *A61K 35/12* (2013.01)

(58) Field of Classification Search
None
See application file for complete search history.

(56) References Cited

U.S. PATENT DOCUMENTS

| | | | |
|---|---|---|---|
| 6,713,246 | B1 | 3/2004 | Reinecke et al. |
| 6,759,188 | B2 | 7/2004 | Reinecke et al. |
| 8,460,227 | B2 | 6/2013 | Bare et al. |
| 2002/0185457 | A1 | 12/2002 | Smith et al. |
| 2006/0177515 | A1 | 8/2006 | Schmieding et al. |
| 2007/0037132 | A1* | 2/2007 | Sukavaneshvar et al. ........ 435/2 |
| 2008/0283474 | A1 | 11/2008 | Leach et al. |
| 2009/0047242 | A1 | 2/2009 | Reinecke et al. |
| 2009/0054865 | A1 | 2/2009 | Brandenburger et al. |
| 2010/0086529 | A1* | 4/2010 | Mohammad et al. ...... 424/93.73 |

FOREIGN PATENT DOCUMENTS

| | | |
|---|---|---|
| DE | 10 2006 005 016 | 8/2007 |
| WO | WO/2008/127639 | 10/2008 |

OTHER PUBLICATIONS

McCarrel et al., Journal of Orthopaedic Research, Aug. 2009, pp. 1033-1042.*
Antonio Frizziero et al., "Autologus Conditioned Serum for the Treatment of Osteoarthritis and Other Possible Applications in Musculoskeletal Disorders", British Medical Bulletin 2013, vol. 105, Jul. 4, 2012, pp. 169-184.
William P. Arend et al.; "IgG Induction of IL-1 Recepto Antagonist Production by Human Monocytes", Immunological Reviews; 1994; pp. 70-78.
L.S. Anderson et al.; "IgG for Intravenous Use, Autologous Serum and Plasma Induce Comparable Interleukin-1 Receptor Antagonist Liberation From Human Mononuclear Cells: An In Vitro Phenomenon Depending Upon Plastic Adherence", Autoimmunity; 1995; vol. 22; pp. 127-133.

* cited by examiner

*Primary Examiner* — Chris R Tate
*Assistant Examiner* — Douglas F White
(74) *Attorney, Agent, or Firm* — Dickstein Shapiro LLP

(57) ABSTRACT

Systems and methods for producing enhanced blood serum with concentrated growth factors and/or prophylactically and therapeutically active proteins. An autologous blood product is obtained from a donor and then incubated into a containment device (sterile container) that includes a source of cells or tissue (for example, autologous, allogeneic, or xenographic tissue, or combinations thereof). The cells from the injected fluid (autologous blood product) interact/incubate with the source of cells or tissue inside the containment device, to produce a serum that is loaded with autologous proteins, growth factors, and cytokines. The autologous blood product may be a fluid and/or composition that includes blood, whole blood, autologous conditioned plasma, platelet-rich plasma, platelet-poor plasma, bone marrow aspirate, bone marrow concentrate and stem cells, among others, and combinations thereof.

12 Claims, 4 Drawing Sheets

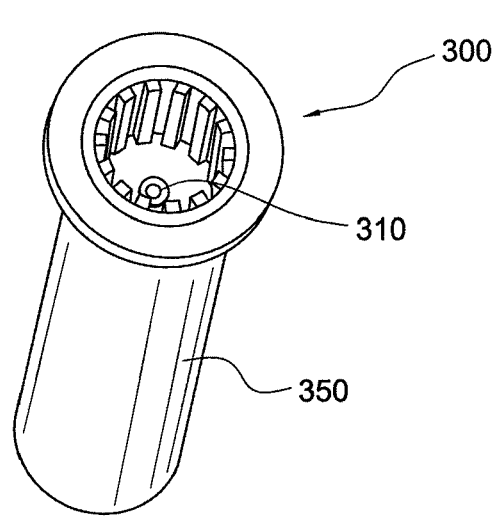
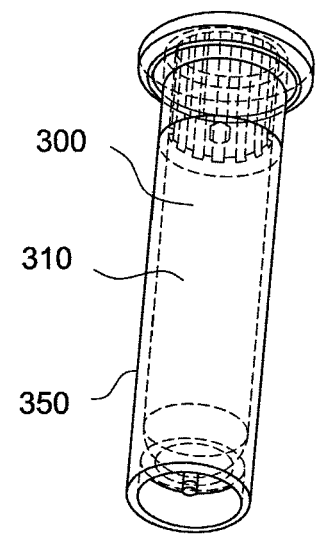
FIG. 4   FIG. 6
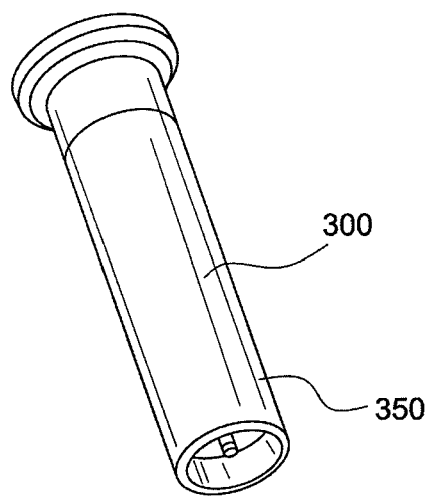
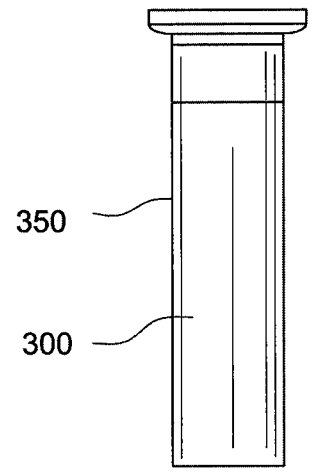
FIG. 5   FIG. 7

ENHANCED AUTOLOGOUS GROWTH FACTOR PRODUCTION AND DELIVERY SYSTEM

CROSS-REFERENCE TO RELATED APPLICATIONS

This application claims the benefit of U.S. Provisional Application No. 61/672,975 filed Jul. 18, 2012, the disclosure of which is incorporated by reference in its entirety herein.

FIELD OF THE INVENTION

The present invention relates to systems and methods for producing autograft or autologous enhanced serum containing prophylactically or therapeutically active proteins.

BACKGROUND OF THE INVENTION

Methods for producing interleukin-1 receptor antagonist ("IL-1Ra") in a syringe are described in U.S. Pat. Nos. 6,759,188; 6,623,472; and 6,713,246, the disclosures of all of which are hereby incorporated by reference in their entirety. These methods require the use of a special syringe to produce the IL-1Ra and do not provide methods for dividing the protein serum containing IL-1Ra or other therapeutically active proteins into portions for long-term storage and/or transportation.

There is a need for devices, systems and techniques that would maximize the innate healing response of the human body by delivering autologous growth factors, cytokines and proteins to a wounded tissue site, without the need for a special syringe.

SUMMARY OF THE INVENTION

The present invention provides methods and systems for producing enhanced serum to be injected at a wounded site. The enhanced serum is obtained by incubating blood/fluid in a simple, sterile container (test tube) together with a source of cells or tissue, for example, an autograft, allograft or xenograft tissue such as collagen. The autograft, allograft or xenograft tissue is loaded in the sterile container and mixed with blood or a fluid. The cells from the injected blood/fluid interact/incubate with the autograft, allograft or xenograft tissue inside the tube to produce a serum that contains autologous proteins, growth factors, and cytokines. The construct is then centrifuged and the serum can be extracted from the tube and injected at a wounded tissue site. Incubation can be conducted at ambient conditions, or at 37° C. between 1 and 24 hours.

The present invention also provides methods of producing enhanced serum to be injected at a wounded site by inter alia the steps of: (i) providing a sterile container and adding at least one of autograft, allograft or xenograft tissue (for example, collagen) in any size and/or shape; (ii) adding a fluid (for example, blood, autologous conditioned plasma, bone marrow aspirate, PRP, PPP, etc) to the autograft, allograft or xenograft tissue; (iii) incubating the fluid with the autograft, allograft or xenograft tissue for about 0-24 hours, preferably between 1 and 24 hours; (iv) subjecting the sterile container to hard spinning to separate cells and tissue from growth factors; (v) withdrawing the concentrated growth factors (could optionally filter out catabolics); and (vi) delivering the concentrated growth factors to a patient (could optionally further mix with ACP and or add a scaffold). The system delivers concentrated growth factors, proteins, and cytokines that are devoid of cells.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 4 illustrates a perspective view of a containment device (incubation device or container) according to yet another exemplary embodiment of the present invention.

FIG. 5 illustrates another perspective view of the containment device of FIG. 4.

FIG. 6 illustrates a perspective, partial cross-sectional view of the containment device of FIG. 4.

FIG. 7 illustrates a front view of the containment device of FIG. 4.

DETAILED DESCRIPTION OF THE EMBODIMENTS

Figure 1A:
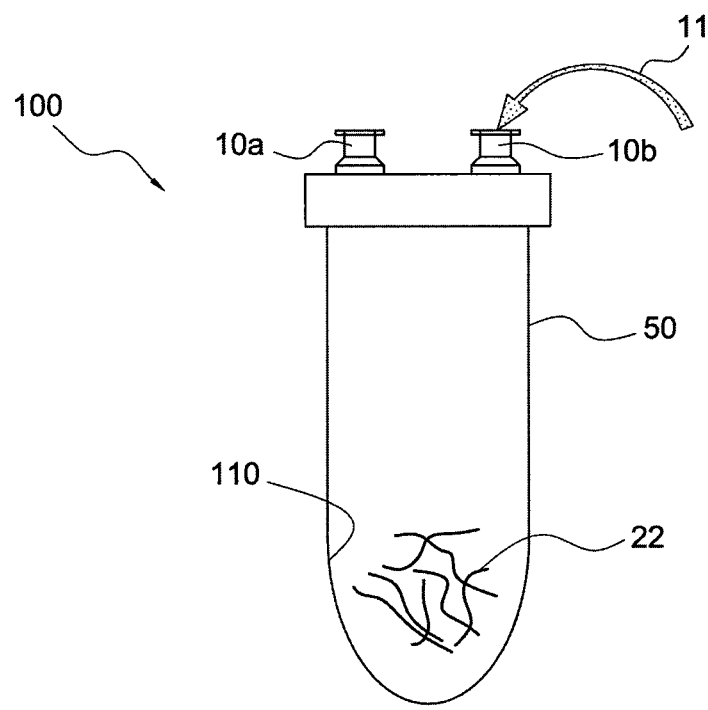
FIGS. 1(a) and 1(b) illustrate a containment system (with a sterile container) according to an exemplary embodiment of the present invention.

The present invention provides systems and methods for producing enhanced blood serum with concentrated growth factors and/or prophylactically and therapeutically active proteins. An autologous blood product or fluid is obtained from a donor and then incubated into a containment device (sterile container) that includes a source of cells or tissue (for example, autologous, allogeneic, or xenographic tissue, or combinations thereof, the tissue being natural, synthetic or composite products tissue). The cells from the injected fluid or autologous blood product interact/incubate with the source of cells or tissue inside the containment device, to produce a serum that is loaded with autologous proteins, growth factors, and cytokines. The serum can be extracted from the containment device and injected at a wounded tissue site. Incubation could be conducted at ambient conditions or at 37° C. between 1 and 24 hours. The autologous blood product may be a fluid and/or composition that includes blood, whole blood, autologous conditioned plasma (ACP), platelet-rich plasma (PRP), platelet-poor plasma (PPP), bone marrow aspirate (BMA), bone marrow concentrate (BMC) and stem cells, among others, and/or combinations thereof.

The present invention also provides methods and systems for producing enhanced autograft or autologous blood serum containing prophylactically or therapeutically active proteins. The enhanced serum is obtained by incubating blood/fluid in a simple, sterile container (test tube) together with a source of cells or tissue, for example, an autograft, allograft or xenograft tissue or material, which may be in natural, synthetic or composite form (or combinations of these forms). The source of cells or tissue is loaded in the sterile container and mixed with blood (for example, whole blood) or a fluid such as autologous conditioned plasma (ACP), platelet-rich plasma (PRP), platelet-poor plasma (PPP), bone marrow aspirate (BMA), bone marrow concentrate (MBC) and stem cells, among others, and/or combinations thereof. The source of cells or tissue is brought together with the fluid/autologous blood product into the sterile container, incubated, and then subjected to hard spinning such as centrifugation, to obtain enhanced growth factors and prophylactically and therapeutically active proteins. The growth factors and prophylactically and therapeutically active proteins may be separated from the source of cells or tissue by collecting a serum rich in those elements.

In an exemplary embodiment, the present invention provides methods and systems for producing enhanced autograft or autologous blood serum containing prophylactically or therapeutically active proteins. The enhanced serum is obtained by incubating blood/fluid in a simple, sterile container (test tube) together with an autograft, allograft or xenograft tissue or material (preferably, collagen). The autograft, allograft or xenograft tissue (autograft, allograft or xenograft material) is loaded in the sterile container and mixed with blood (whole blood) or a fluid such as autologous conditioned plasma (ACP), platelet-rich plasma (PRP), platelet-poor plasma (PPP), bone marrow aspirate (BMA), bone marrow concentrate (MBC) and stem cells, among others, and combinations thereof.

In an exemplary embodiment, the invention uses the sterile container and method steps detailed in US 2006/0177515, the disclosure of which is incorporated by reference in its entirety herewith, but instead of having the beads provided in the test tube (incubation tube), the tube has a source of cells or tissue, i.e., an autograft, allograft or xenograft tissue (preferably collagen). Thus, the device utilizes an incubation tube as disclosed in US 2006/0177515, but substitutes autologous, allogeneic, or xenographic tissue, or even synthetic or composite products tissue, for the beads inside the tube.

Any type of fluid/composition can be injected into the device. The fluid may be an autologous blood product and/or composition that includes blood, whole blood, autologous conditioned plasma, platelet-rich plasma, platelet-poor plasma, bone marrow aspirate, bone marrow concentrate and stem cells, among others, and combinations thereof. The cells from the injected fluid interact/incubate with the tissue inside the tube, to produce a serum that is loaded with autologous proteins, growth factors, and cytokines. The serum can be extracted from the tube and injected at a wounded tissue site. Incubation can be conducted at ambient conditions or at 37° C. between 1 and 24 hours.

In a specific embodiment only, the incubation may be conducted with a collagen construct. The collagen can be of autograftic, allograftic, or xenograftic origination. The collagen can be provided in natural form, partially natural form, or may even be produced synthetically. The collagen can be obtained, purified, or derived from connective tissue or fibrous tissue (for example, tendons, ligaments, skin, cartilage, bone, intervertebral tissue, among others). The collagen may be any of the Types I-V collagen, preferably Type I and Type II collagen. The physical construct of the collagen could be, but is not limited to strips, granules, powder, cylinder(s), scaffolding, mesh, etc., or any combination thereof.

Figure 1B:
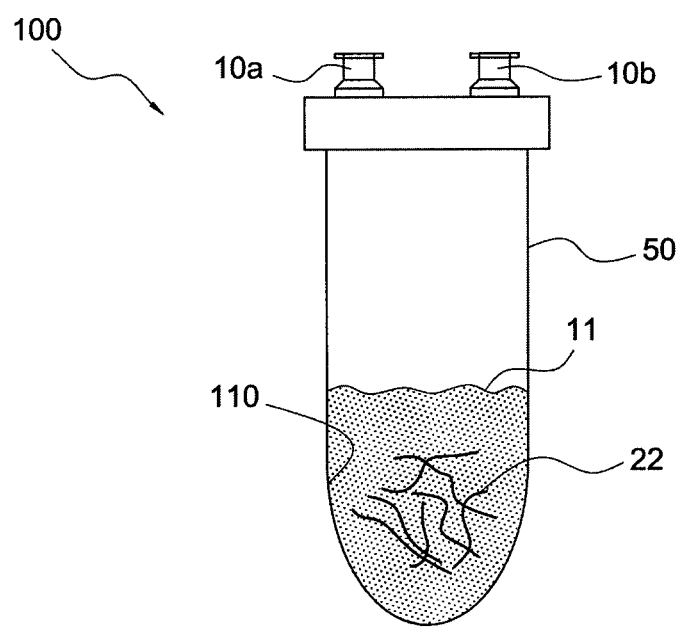

Reference is now made to FIGS. 1(a) and 1(b) which illustrate system 100 of the present invention comprising containment device 50 (sterile container 50) which is an exemplary test tube. The sterile container 50 of FIG. 1(a) is modified to allow containment of blood/fluid and material, and mixing of the blood/fluid with the material, as detailed below. The containment device 50 is a ported system with luer connections 10a, 10b that allow for delivery of an autologous fluid 11 (blood such as whole blood, autologous conditioned plasma (ACP), platelet-rich plasma (PRP), platelet-poor plasma (PPP), bone marrow aspirate (BMA), bone marrow concentrate (MBC), stem cells or combinations thereof) and holding of a source of cells or tissue 22, for example, autologous, allogenic, or xenographic tissue 22. In a preferred embodiment, the source of cells or tissue 22 is synthetic or purified collagen 22. FIG. 1(b) illustrates containment device 50 with autologous blood product (fluid) 11 brought into contact with source of cells or tissue 22 (collagen 22).

Containment device 50 may be a sterile container of any suitable size or configuration (e.g., vial, capped container, closed tube) and is preferably made of a material that can be subjected to sterilization (e.g., chemical sterilization, autoclave). For example, the container 50 can be made of any suitable glass, ceramic, or plastic material (e.g., polystyrene, polypropylene, polycarbonate).

The surface area of the inner surface 110 of the sterile container 50, or a portion thereof, can be increased by adding and/or coating the inner surface 110 of the container 50 with additional coating materials that increase the surface area, providing additional attachments for adherence by blood monocytes (not shown), which stimulates the monocytes to produce therapeutically or prophylactically active proteins such as, for example, IL-1Ra. In an exemplary embodiment only, the inner surface 110 of the container 50, or a portion thereof, can be coated with an anti-coagulant such as heparin.

FIGS. 1(a) and 1(b) also illustrate source of cells or tissue 22, for example, autologous, allogenic, or xenographic tissue/ material 22, contained within the sterile container 50. The autograft, allograft or xenograft tissue 22 is loaded in the sterile container 50 and mixed with blood/fluid 11 (FIG. 1(b)). In an exemplary embodiment, autologous, allogenic, or xenographic tissue 22 may be collagen 22 which may be synthetic or natural, and which may be provided in the form of strips, for example.

As noted, the collagen 22 can be of autograftic, allograftic, xenograftic origination, or may even be produced synthetically. The collagen 22 can be obtained, purified, or derived from connective tissue or fibrous tissue (for example, tendons, ligaments, skin, cartilage, bone, intervertebral tissue, among others). The collagen 22 may be any of the Types I-V collagen, preferably Type I and Type II collagen. The physical construct of the collagen 22 could be, but is not limited to strips, granules, powder, cylinder(s), scaffolding, etc.

In one embodiment of the invention, autologous fluid 11 (for example, blood 11) is obtained from a patient (by withdrawing the fluid 11 with a syringe, for example) and then injected into sterile container 50 containing autologous, allogeneic, or xenographic tissue 22 (for example, collagen 22). After injection of the autologous fluid 11 through one of the luer ports 10a, 10b, the fluid 11 is mixed with the autologous, allogeneic, or xenographic tissue 22. After mixing, the fluid can be (i) immediately removed; or (ii) incubated for up to 24 hours (between 1 and 24 hours) at ambient conditions or 37° C., and then a serum extracted; or (iii) incubated for up to 24 hours (between 1 and 24 hours) at ambient conditions or 37° C., then centrifuged, and then a serum extracted. The autologous, allogeneic, or xenographic material 22 is left in the container.

The incubation in steps (ii) and (iii) may be conducted at a temperature suitable to induce production of growth factors, and/or prophylactically or therapeutically active proteins (e.g., IL-1Ra, interleukin 4, interleukin 10, and TGF beta). In an exemplary embodiment only, the incubation is conducted at temperatures from about 35 to 39° C., more preferably from about 36° C. to about 38° C., most preferably at 37° C.

The autologous fluid 11 (the cells within the fluid) interact with the material 22 to produce growth factors, cytokines and proteins (that will be provided at a wounded tissue site). These proteins "float" in the surrounding fluid and can be retrieved/retracted for delivery at an injured tissue site.

Figure 2B:
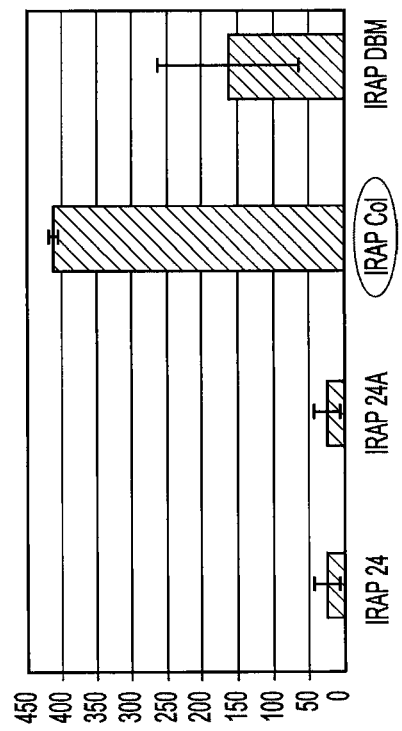
FIG. 2(b) illustrates a graph depicting concentrations for IL-1beta with different incubation materials (including collagen strips) using an exemplary construct.
Figure 2A:
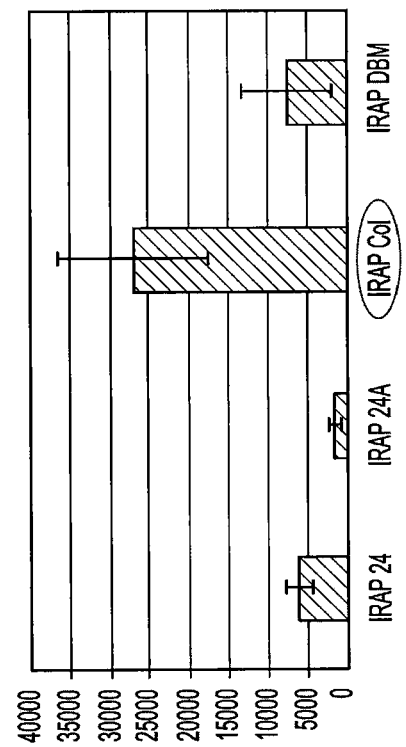
FIG. 2(a) illustrates a graph depicting concentrations for IL-1Ra with different incubation materials (including collagen strips) using an exemplary construct.

Reference is now made to FIGS. 2(*a*) and 2(*b*) which illustrate two graphs depicting concentrations for IL-1Ra (FIG. 2(*a*)) and IL-1beta (FIG. 2(*b*)) with different incubation constructs and materials (all using an exemplary IRAP II construct). Each graph illustrates the levels of IL-1Ra concentration (FIG. 2(*a*)) and IL-1beta concentration (FIG. 2(*b*)) for four different exemplary constructs: IRAP 24 (an IRAP II construct with 24 hours incubation); IRAP 24A (an IRAP II construct with ACDA and 24 hours incubation); IRAP Col (an IRAP II Tube with collagen and no beads and 24 hours incubation); and IRAP DBM (an IRAP II Tube with DBM and no beads and 24 hours incubation).

The two graphs clearly evidence the increase in the concentrations for both IL-1Ra and IL-1 beta with a construct having collagen (i.e., the collagen group under "IRAP Col"). The collagen group produced significantly higher amounts of monocytic-derived growth factors (GFs), and increased level of catabolic and anabolic activity (as a result of the natural injury response and monocyte exposure to collagen).

Figure 3:
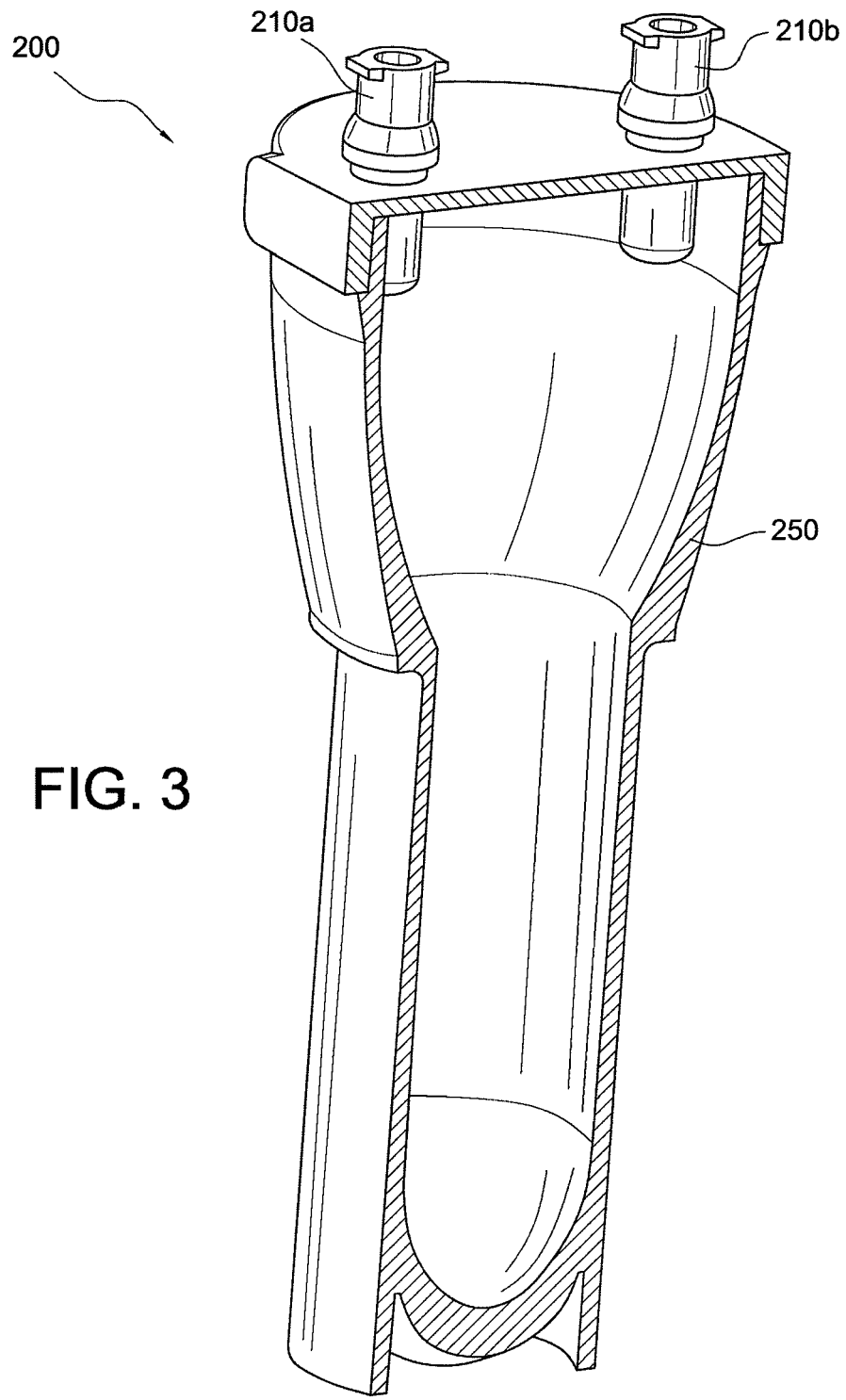
FIG. 3 illustrates a cross-sectional perspective view of a containment device (incubation device or sterile container) according to another exemplary embodiment of the present invention.

FIG. 3 illustrates another exemplary embodiment of incubations system 200 with containment device 250 (sterile container 250) which is similar to the containment device 50 of FIGS. 1(*a*) and 1(*b*) in that it is also a ported system with luer connections/ports 210*a*, 210*b* that allow for delivery of an autologous fluid 11 and holding of autologous, allogeneic, or xenographic tissue 22, but differs in that it has a specific design, i.e., a modified test tube design. Incubation device 250 can be made of any suitable glass, ceramic, or plastic material (e.g., polystyrene, polypropylene, polycarbonate).

FIGS. 4-8 illustrate another embodiment of system 300 of the present invention which includes incubation device 350 (containment device or sterile container 350) which is similar to the containment device 50 of FIGS. 1(*a*) and 1(*b*) in that it allows introduction of a fluid (for example, blood (whole blood), autologous conditioned plasma (ACP), platelet-rich plasma (PRP), platelet-poor plasma (PPP), bone marrow aspirate (BMA), bone marrow concentrate (MBC), stem cells or combinations thereof) into container 350 with at least one of autograft, allograft or xenograft tissue or material (for example, collagen) but differs in that it has a specific design, i.e., a modified tube design with only one centrally located port/lumen 310 (FIG. 4). Containment device (incubation device) 350 can be made of any suitable glass, ceramic, or plastic material (e.g., polystyrene, polypropylene, polycarbonate). The inner surface 310 (FIG. 6) of the device 350, or a portion thereof, may be also increased by adding and/or coating the inner surface 310 of the container 350 with additional coating materials that increase the surface area, providing additional attachments for adherence by blood monocytes (not shown), which stimulates the monocytes to produce therapeutically or prophylactically active proteins such as, for example, IL-1Ra. In an exemplary embodiment only, the inner surface 310 of the container 350, or a portion thereof, can be coated with an anti-coagulant such as heparin.

A method of producing enhanced serum to be injected at a wounded site comprises the steps of: (i) providing a sterile container 50, 250, 350 and adding at least one of autograft, allograft or xenograft tissue or material 22 (for example, collagen 22) in any size and/or shape; (ii) adding a fluid 11 (for example, an autologous blood product which may include blood, whole blood, autologous conditioned plasma, platelet-rich plasma, platelet-poor plasma, bone marrow aspirate, bone marrow concentrate and stem cells, among others, and combinations thereof) to the autograft, allograft or xenograft tissue or material 22 to form system 100, 200, 300; (iii) incubating the fluid 11 with the autograft, allograft or xenograft tissue or material 22 for about 0-24 hours, preferably between 1 to 24 hours; (iv) subjecting the sterile container 50, 250, 350 to hard spinning to separate cells and tissue from growth factors; (v) withdrawing the concentrated growth factors (could optionally filter out catabolics); and (vi) delivering the concentrated growth factors to a patient (could optionally further mix with ACP and or add a scaffold).

Preferred embodiments of the invention also provide methods of treating a patient by administering enhanced serum containing the prophylactically or therapeutically active proteins to a patient in need of treatment. For example, patients suffering from osteoarthritis and tendonitis may benefit from such treatment. In exemplary veterinary medicine applications, serum from a donor herd of horses can be used to produce prophylactically or therapeutically active proteins for administration to horses in need of treatment.

If necessary, the protein serum component may be divided and stored in a container (separate from the containment device 50, 250, 350). The container can be frozen to preserve the serum for long or short term storage and/or for transportation of the serum. After thawing, a portion of the serum (e.g., one container or vial) of serum can be administered (e.g., via injection or perfusion) by an orthopedic surgeon into a patient, for example, at a specific site (e.g., specific joint, tendon, muscle, or other soft tissue) to treat or reduce the symptoms associated with a disease condition (e.g., osteoarthritis or tendonitis).

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:

1. A method of producing blood serum containing concentrated growth factors, comprising the steps of:
   I. incubating:
      a) an autologous blood product selected from the group consisting of platelet rich plasma, bone marrow aspirate, bone marrow concentrate, and combinations thereof, with
      b) a collagen construct wherein the collagen construct comprises Type I or Type II collagen obtained, purified, or derived from connective tissue selected from the group consisting of tendons, ligaments, cartilage, and bone; wherein the incubating is at a temperature about 35° C. to about 39° C. in a container for a suitable time to produce increased levels of growth factors; and
   II. subjecting the container to hard spinning to separate cells and tissue from serum; and
   III. extracting said serum containing concentrated growth factors from the container.

2. The method of claim 1, wherein the collagen is autograftic, allograftic, or xenograftic tissue, or combinations thereof.

3. The method of claim 1, wherein the step of incubating is conducted between 1 and 24 hours.

4. The method of claim 1, wherein the step of incubating is conducted at a temperature of about 37° C.

5. The method of claim 1, wherein the autologous blood product is bone marrow aspirate.

6. The method of claim 1, wherein the autologous blood product is platelet-rich plasma.

7. The method of claim 2, wherein the collagen construct comprises autograftic collagen.

8. The method of claim 2, wherein the collagen construct comprises allograftic collagen.

9. The method of claim 1, wherein the collagen construct comprises Type II collagen.

10. The method of claim 1, wherein the collagen construct is strips, granules, powder, scaffolding, mesh, or combinations thereof.

11. The method of claim 1 further comprising freezing at least a portion of the serum.

12. The method of claim 1, wherein at least a portion of an inner surface of the container is coated with an anti-coagulant.

* * * * *